United States Patent [19]

Man

[11] Patent Number: Plant 7,037

[45] Date of Patent: Sep. 19, 1989

[54] DISTINCT VARIETY OF BEGONIA PLANT NAMED DANJA

[75] Inventor: Jan Man, Lisse, Netherlands

[73] Assignee: Oglevee Ltd., Connellsville, Pa.

[21] Appl. No.: 251,654

[22] Filed: Sep. 29, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new begonia variety is characterized by its strong growth, abundant flowering, and soft pastel yellow flower color.

1 Drawing Sheet

BACKGROUND OF THE NEW PLANT

The present invention comprises a new and distinct cultivar of *Begonia*×*hiemalis* known by the varietal name of Danja. The new cultivar resulted from the self pollination of the cultivar Rosalie (U.S. Plant Pat. No. 6,321). The new cultivar has the same habit and growing characteristics as Rosalie but has a different leaf shape and flower color. The new variety has a leaf shape with an acute tip with an irregularity lobed attachment whereas Rosalie has a shape of an ovate tip with an oblique petal attachment. The new variety has a flower color which is soft pastel yellow as compared to the pastel peach with pink tones of the flower of the variety Rosalie.

The new cultivar was discovered in April of 1985 at Limaplant, b.v. in Lisse, Holland, was first asexually reproduced by cuttings at Limaplant, b.v. in Lisse, Holland and has been asexually reproduced by cuttings for Oglevee Limited in Connellsville, Pa. It has been found to retain its distinctive characteristics through successive propagations.

The new cultivar is generally characterized by its strong growth and abundant flowering. The plant has short compact internodes with good basal branching. The strong stems give good self support. The soft pastel yellow coloring fulfills a market need.

The new cultivar, when grown in a greenhouse in Connellsville, Pa., has a response time of 9 to 10 weeks from a well-rooted cutting to a flowering finished plant in a six inch pot (no pinch).

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out for Oglevee Limited in Connellsville, Pa. The plant history was taken on ten week plants blossomed under natural light in a greenhouse and grown under temperature conditions of 62° F. at night and 68° F. during the day. The plants were potted in July of 1987 in a peat-lite mix and fertilized with a mixture of 20N-10P-20K. Color readings were taken indoors under 200 footcandles of cool white fluorescent tubes. Color references are to the R.H.S. Colour Chart of The Royal Horticultural Society of London, unless noted differently.

Botanical classification: *Begonia*×*hiemalis*

Flower:

*Fully expanded.*—6 cm. in diameter; side view: flat and oval appearance.

*Borne.*—Compound dichasium with opposite bracts at the base of each flower cluster. The bracts are characterized by an obtuse base with a slightly undulate margin, and occur at bifurcation of the inflorescence.

*Stems.*—Strong upright stems; average stem width 1.0 cm. Color: Yellow-green group 145C.

*Form.*—Male flower, double. Each flower has 2 sepals, 6 petals and, 17 petaloids (each group may vary ± 1 on the structure). Female flowers tend to have only 2 sepals, 4 petals, and 3 petaloids.

*Permanence.*—Very long lasting bloom, average life span of 2 weeks.

Color:

*Tonality from a distance.*—The flower color is a soft pastel yellow.

*Front of petals.*—Fully mature petals are characterized by an outer margin having a color yellow group 8D and the center having a color yellow group 8B.

*Reverse of petals.*—Fully mature and expanded petals are characterized by a translucent color of yellow group 8D.

*Calyx.*—Consists of 2 sepals (outer floral envelopes). Front—yellow-group 8D and as you move toward the apex of the petal, color becomes translucent. Reverse: this flower part in the bud stage has slight pink tones in its center. The pink disappears by the time the flower fully matures. The color of the calyx in the bud stage is characterized by the color 8D.

*Bract.*—Characterized by margin color red group 45C lightening in intensity as base is approached.

*Throat.*—None.

*Discoloration.*—None.

*Other comments.*—Flower color is a very light yellow with a high degree of consistency in flower color. Both male and female flowers are the same color.

Petals:

*Texture.*—Crepe paper like (gentle crinkles).

*Appearance.*—Translucent yellow color.

*Arrangement.*—Semi to fully double.

*Persistence.*—Very good flower response, produces high number of buds.

Reproductive organs: None observed with reproductive organs formed into petaloids.

Plant:

*Form.*—Short and compact; internodes; good basal branching; strong stems; good self-support.

*Growth.*—Very vigorous; upright growth habit.

*Height from soil line.*—25 to 28 cm. in 10 weeks (no pinch, no cycocel).

*Spread.*—25 to 30 cm. in 10 weeks (no pinch, no cycocel).

Foliage:

*Size.*—Average size of leaves 4 nodes above the soil line in 16 cm long by 11 cm wide.

*Quantity.*—Abundant.

*Shape.*—Acute tip with irregularly lobed attachment; edge is doubly serrated.

*Top side.*—Green group 137B.

*Underside.*—Green group 148C; shiny and smooth.

*Ribs and veins.*—Smooth on top, raised on lower side. Lower side of veins only area where tricomes (hair) appear.

*Rib and vein color.*—Top side: yellow-green group 150D; bottom side: yellow-green group 147D.

*Margin.*—None.

*Stipules.*—Color: yellow-green group 145C.

I claim:

1. A new and distinct variety of begonia characterized by its strong growth, abundant flowering, and soft pastel yellow flower color as herein shown and described.

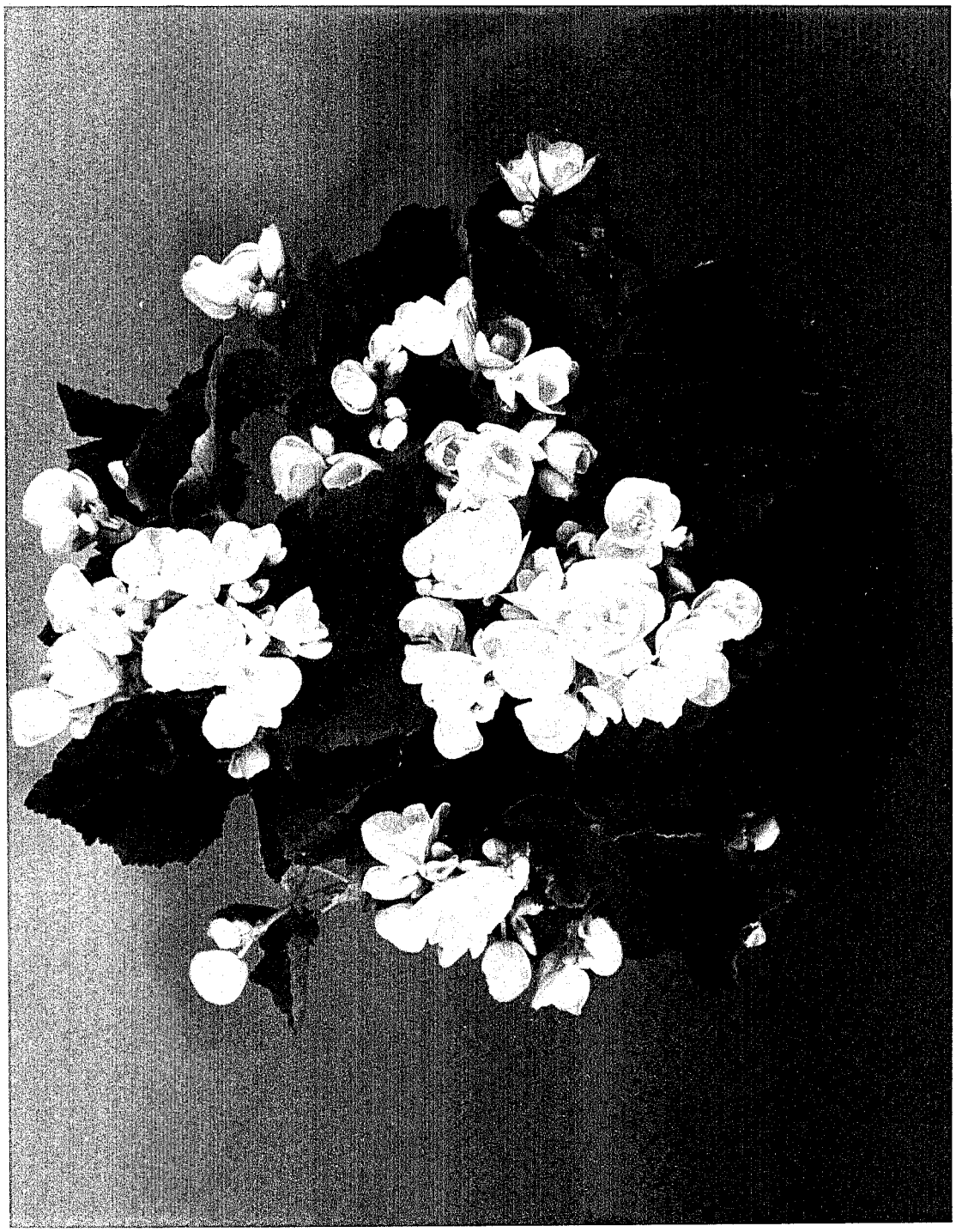

* * * * *